United States Patent
Williamson, IV et al.

[11] Patent Number: 6,080,173
[45] Date of Patent: Jun. 27, 2000

[54] TISSUE PUNCHING INSTRUMENT

[75] Inventors: Warren P. Williamson, IV, Loveland; Craig B. Berky, Milford, both of Ohio; Paul A. Spence, Louisville, Ky.; Mark Ortiz, Milford, Ohio

[73] Assignee: IDx Medical Ltd., Loveland, Ohio

[21] Appl. No.: 09/318,866

[22] Filed: May 26, 1999

[51] Int. Cl.$^7$ .................................................. A61B 17/32
[52] U.S. Cl. ........................... 606/184; 606/185; 600/567
[58] Field of Search .................................. 606/184, 185; 604/22; 600/564–569

[56] References Cited

U.S. PATENT DOCUMENTS

| | | | |
|---|---|---|---|
| 4,018,228 | 4/1977 | Gossen | 606/184 |
| 4,216,776 | 8/1980 | Downie et al. | 606/184 |
| 5,827,316 | 10/1998 | Young et al. | 606/185 |
| 5,972,014 | 10/1999 | Nevins | 606/185 |

*Primary Examiner*—Michael Buiz
*Assistant Examiner*—William W. Lewis
*Attorney, Agent, or Firm*—Terry M Gernstein

[57] ABSTRACT

A surgical punch prevents tissue debris associated with punching a hole in a patient's tissue, such as an aorta during an anastomosis procedure, from reentering the patient's bloodstream. The punch includes elements that move the debris away from the cutting site and then capture that debris inside the instrument. The punch also includes means for aligning the punch with the selected site and for atraumatically holding the tissue prior to cutting. Various means for moving the tissue debris and for trapping the tissue debris in the instrument are also disclosed.

34 Claims, 11 Drawing Sheets

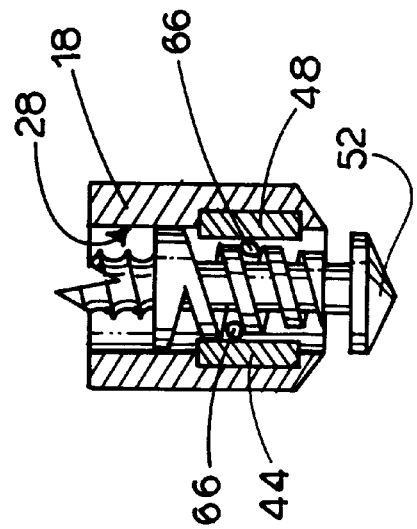
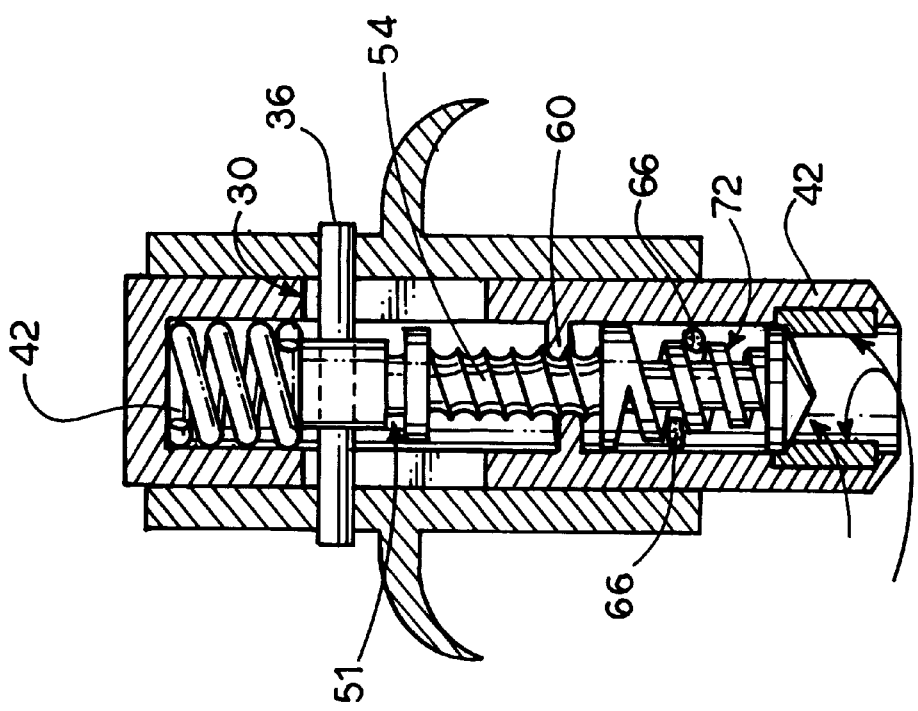
FIG. 4.
FIG. 3.

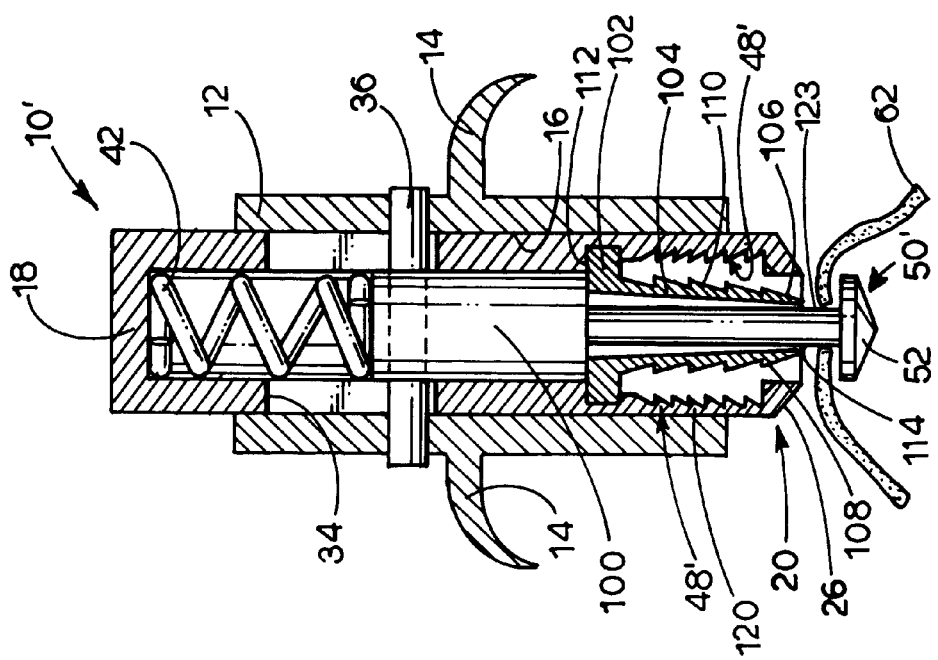
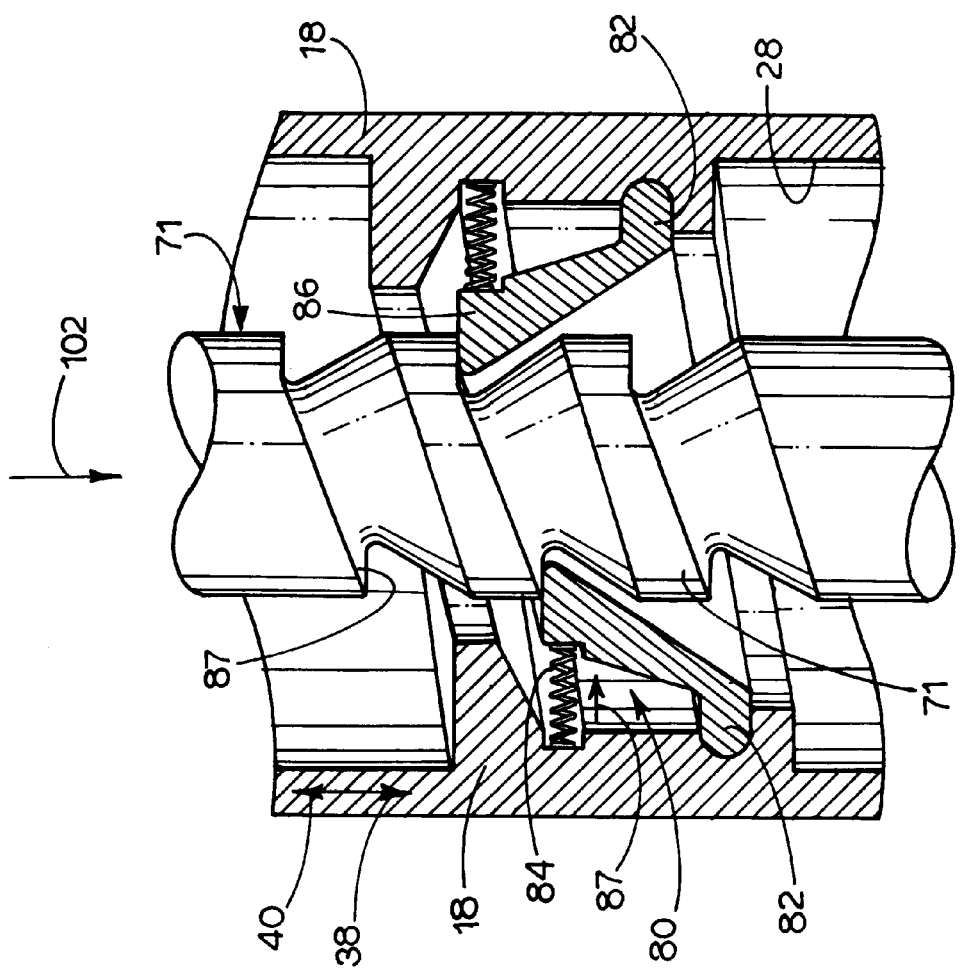
FIG. 5.
FIG. 4A.

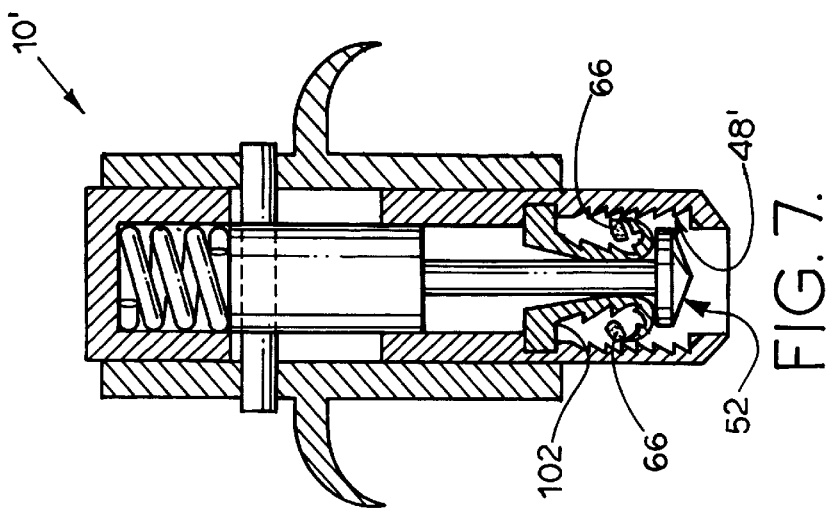
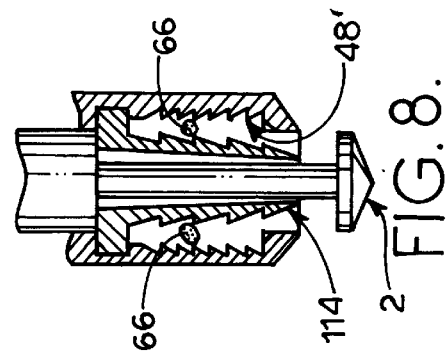
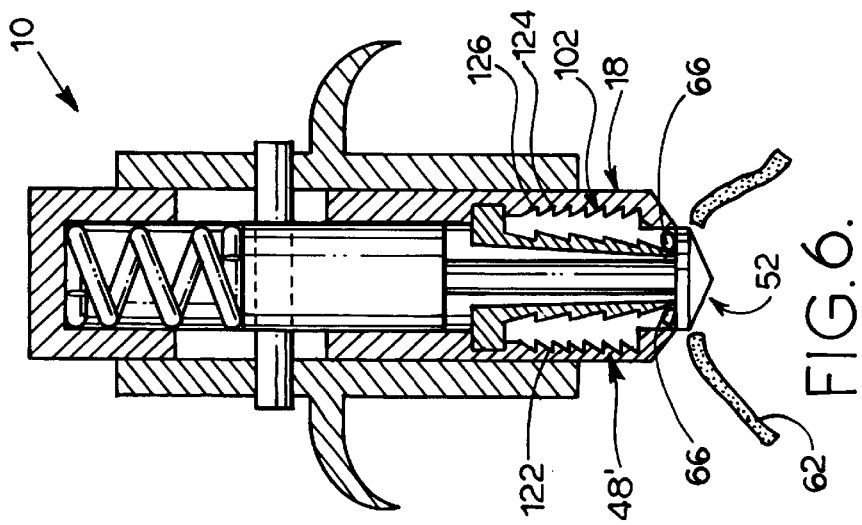

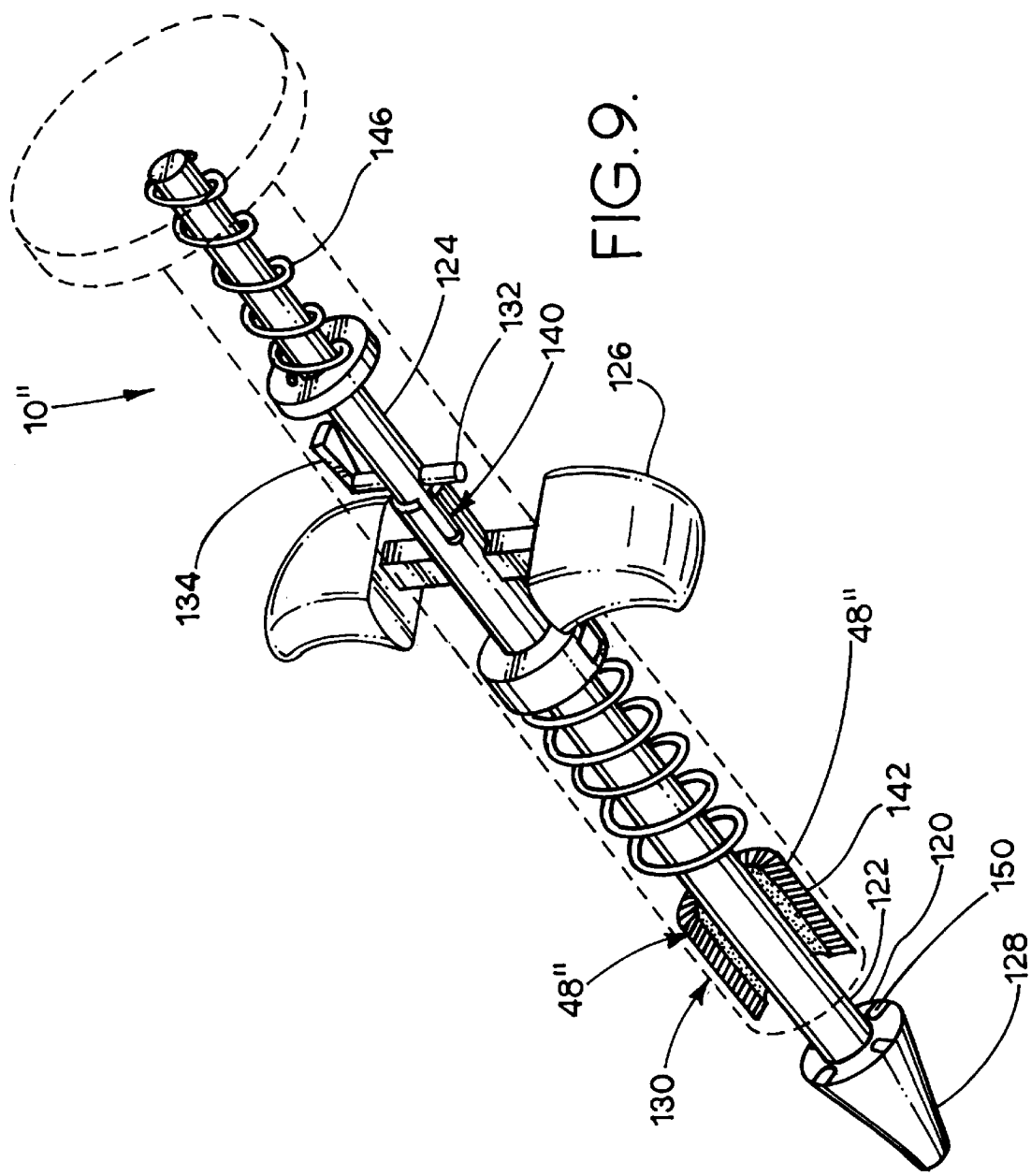

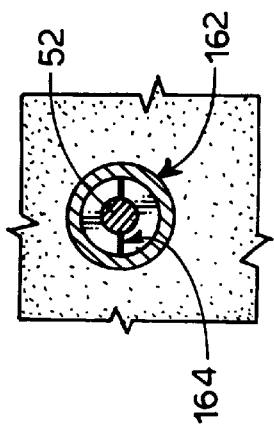
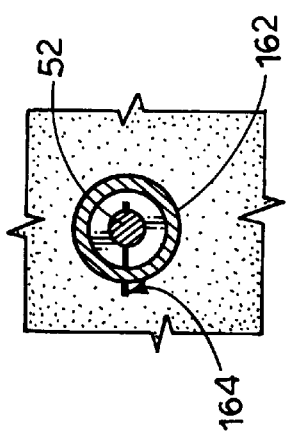
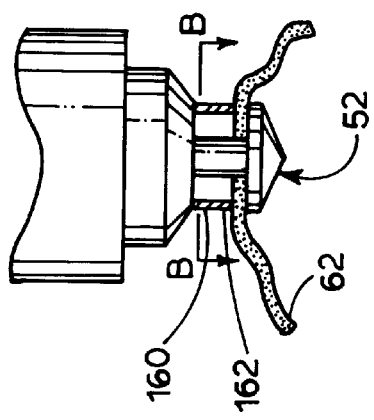
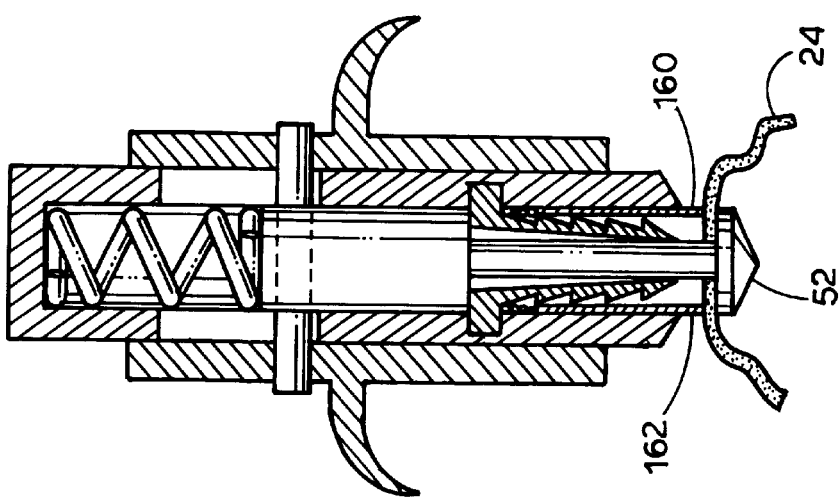

SECTION A-A

SECTION A-A

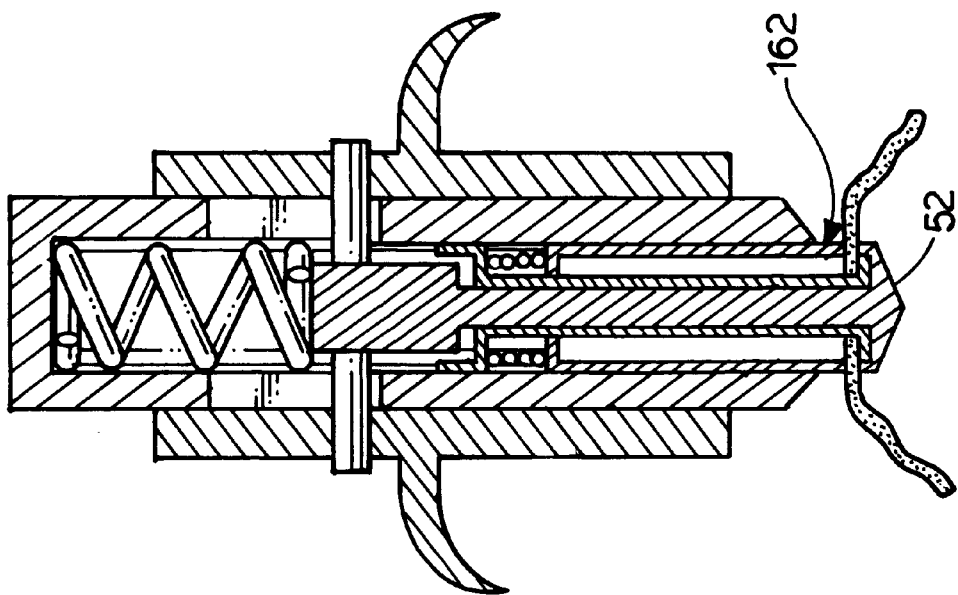
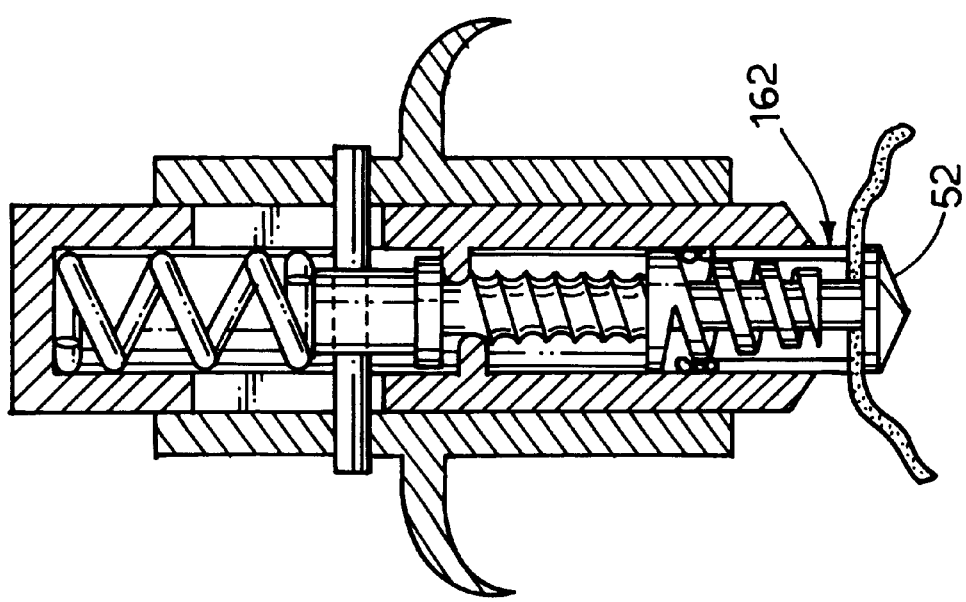

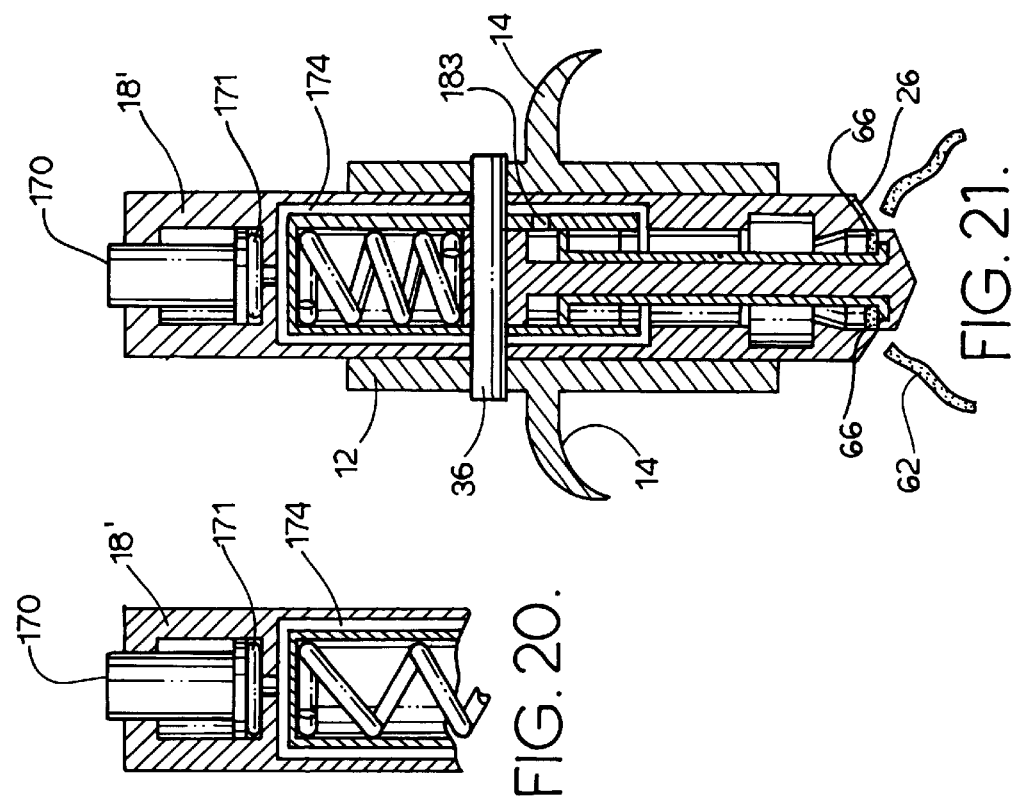
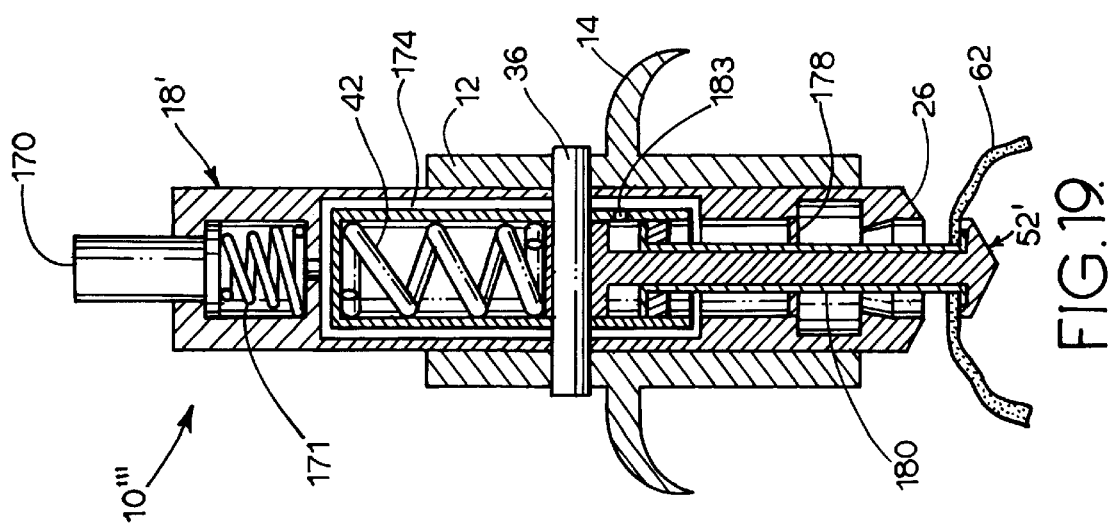
FIG. 21.
FIG. 20.
FIG. 19.

TISSUE PUNCHING INSTRUMENT

TECHNICAL FIELD OF THE INVENTION

The present invention relates to the general art of surgery, and to the particular field of surgical devices, including tissue punches.

BACKGROUND OF THE INVENTION

Coronary bypass surgery is frequently performed in the treatment of coronary artery disease. When native coronary arteries are obstructed (coronary artery disease) bypasses can be created by shunting flow from a large vessel such as the aorta to a part of the obstructed blood vessel downstream of the obstruction. As is known in this art, a variety of conduits (tubes) can be used to carry this bypass flow, including portions of the patient's own arteries and veins or artificial materials. Co-pending patent application Ser. No. 08/200,615 filed on Nov. 27, 1998 and U.S. Pat. No. 5,868,763, the disclosures of which are fully incorporated herein by reference, disclose means and methods for performing an anastomosis which can be used in such bypass surgery.

When a conduit is connected to the aorta (anastomosed) the process is initiated by defining an incision through the wall of the aorta and then punching a circular hole in the wall of the aorta adjacent to the incision to define a widely flowing junction point. A surgical tissue punch is generally used to define this hole. In using the surgical punch, the surgeon first stabs a small slit in the wall of the aorta and then inserts the punch through the slit. The punch is then deployed and a circular or elliptical hole is created. The aorta is sewn to the conduit adjacent to this hole.

The art contains several surgical punches which have been extensively used. For example, some punches include a small cone-shaped plunger which has been machined to have a very precise sharp right-angled surface. Proximally to the cone there is a stem or neck which is smaller than the largest diameter of the cone. The stem increases in diameter up to a body size that rides inside the body of the punch housing. The punch housing is a steel tube which at the distal end thereof has been sharpened with an angular surface, angling from the outer surface of the tube to an inner bore of the tube. The plunger and the housing are assembled together with a spring-loaded hand plunger whereby the outer tube is biased toward the plunger. Tissue introduced between the plunger and the housing will be sheared off during operation of the punch.

Current punches have several drawbacks. For example, it may take several deployments of the punch to create a desired hole. The tissue that the surgeon contemplates removing may slip away from the cutting blade and only a part of that tissue will be removed. A number of deployments are thus necessary to fully remove all of the tissue necessary to complete the procedure.

Disposal of debris is yet another problem with known punches. As material is cut, tissue pieces are formed and must be carefully and completely removed from the patient. Should a piece of tissue fall back inside the aorta it will be carried away by the patient's blood circulation and may result in an obstruction of a vessel. This process (embolization) can be fatal or can cause serious damage to a patient, particularly if the debris obstructs a cerebral (stroke) or coronary (heart attack) vessel. Current devices draw the cut material into the barrel of the device; however, the punch must be cleaned manually after each deployment to ensure that no material is lost or remains inside the patient. After tissue is cut using known punches, the plunger of the punch must be extended beyond the punch housing exposing the plunger shaft and the debris. The shaft is then manually cleaned and made ready for the next punching operation. This cleaning process is time consuming and can lead to errors. Therefore, there is a need for a tissue punching instrument which does not require this extra step of cleaning out the debris. While attempts have been made to produce a self-cleaning punch, these self-cleaning punches are often difficult to handle and control and may have elements associated therewith that create unwanted clutter at the operating site.

Bypass surgery usually requires the creation of multiple holes in a patient's aorta for junction sites and each defect requires multiple activations of the punch. Therefore, there is a need for a reliable and self-cleaning surgical tissue punching instrument. Still further, given the need to ensure proper and complete removal of debris from the surgical site in these procedures, there is a need for a surgical punch in which debris is removed from the surgical site in a manner that does not interfere with operation or movement of the punch.

An additional drawback associated with some known surgical punches is their tendency to rip the vessel walls during the punching process. This is most often caused by improper clearances between the punch plunger and the punch body. In addition, if the punch is slid too far to one side of the initial aortatomy slit, the slit will remain on the opposite side of the punch. This is not only very hard to see, but it may also create a leak site at the final anastomosis. Therefore, there is a need to hold the plunger stem of a punching instrument centered in the slit to prevent the slit from extending beyond the punch body. Still further, there is a need for a surgical punch which allows the surgeon to see the relationshhip between the punch cut area and the access site during the procedure.

OBJECTS OF THE INVENTION

It is a main object of the present invention to provide a surgical tissue punch that prevents surgical debris from reentering the patient's bloodstream.

It is another object of the present invention to provide a surgical tissue punch that can trap surgical debris within the punching instrument.

It is another object of the present invention to provide a surgical tissue punch that can atraumatically hold the tissue being punched prior to cutting.

It is another object of the present invention to provide a surgical tissue punch that can actively trap tissue debris.

It is another object of the present invention to provide a surgical tissue punch that passively traps tissue debris.

It is another object of the invention to provide a surgical punch that can use a vacuum source to trap tissue debris.

It is another object of the present invention to provide a surgical tissue punch that can securely hold tissue debris before that debris is transferred into a trapping element.

SUMMARY OF THE INVENTION

These, and other, objects are achieved by a surgical tissue punch, also referred to herein as a tissue punching instrument, that traps and contains tissue debris thereby allowing the surgeon to keep the debris clear of the vessel lumen and prevents the tissue debris from reentering the patient's bloodstream. The punch also has a tissue retaining system that will hold the tissue in an atraumatic manner to improve the quality of the cut. The device of the present invention also has sightlines whereby the surgeon will be able to see the relationship between the punch-cut area and the access slit thereby improving the accuracy of the punching procedure.

BRIEF DESCRIPTION OF THE DRAWING FIGURES

Other objects, features and advantages of the invention will become apparent from a consideration of the following detailed description and the accompanying drawings.

FIG. 3 is a view of the punch in a second configuration.

FIG. 4 is a view of the distal end of the punch when the punch is in the first configuration.

FIG. 4a shows the elements for controlling movement of the punch.

FIG. 5 is a view of a second form of the punch in a first configuration.

FIG. 6 is a view of the second form of the punch in an intermediate configuration.

FIG. 7 is a view of the second form of the punch in a second configuration.

FIG. 8 is a view of the distal end of the second form of the punch when the punch is in the first configuration.

FIG. 9 is a perspective view of yet another form of the punch of the present invention.

FIG. 10 shows another form of the punch of the present invention.

FIG. 11 shows a means for atraumatically holding tissue in place during a punching process.

FIG. 12 is a view along line B—B of FIG. 11 when the punch is properly positioned.

FIG. 13 is a view along Section line B—B of FIG. 11 when the punch is not properly positioned.

FIG. 17 shows yet another form of the punch of the present invention.

FIG. 18 shows yet another form of the punch of the present invention.

FIG. 19 shows yet another form of the punch of the present invention.

FIG. 20 shows the proximal end of the FIG. 19 punch.

FIG. 21 shows the FIG. 19 punch in an intermediate, tissue cutting, configuration.

DETAILED DESCRIPTION OF THE PREFERRED EMBODIMENT OF THE INVENTION

Figure 2:
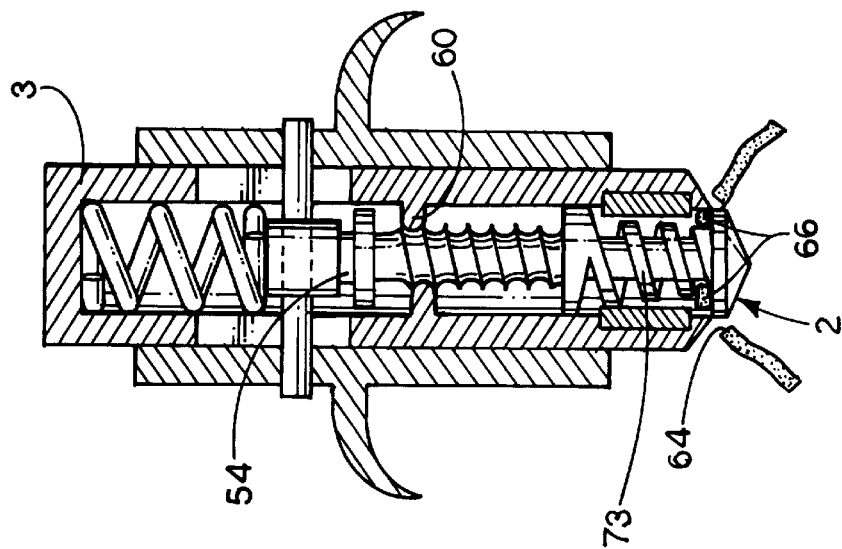
FIG. 2 is a view of the punch in an intermediate configuration.

Shown in FIGS. 1–4 is a tissue punch 10 forming a first form of the device of the present invention. Punch 10 includes an outer body 12 which is cylindrical and includes a finger-engaging element 14. Outer body 12 is hollow and includes a central bore 16 in which cylindrical plunger body 18 is slidably located. Plunger body 18 includes a distal end 20 and a proximal end 22 on which a surgeon places his or her thumb during operation of punch 10. A tissue cutting edge 26 is formed on the distal end of plunger body 18 and the plunger body is hollow with a central bore 28 extending from distal end 20 to proximal end 22. A transverse bore 30 is defined in the wall of housing 12 and a cutout 34 is defined on diametrically opposite sides of plunger body 18 to define openings 34a and 34b shown in FIG. 1. A cross pin 36 is mounted on outer housing 12 and extends through openings 34a and 34b. Cross pin 36 is stationary with respect to outer housing 12 with plunger body 18 being movable with respect to outer housing 12 in directions 38 and 40. A return spring 42 is housed in plunger body 18 and has one end abutting a spring rest 44 mounted on cross pin 36 and another end abutting inner surface 46 of plunger body 18 adjacent to proximal end 22 thereof. Spring 42 is set to bias plunger body 18 in direction 40. A tissue debris catching and holding means 48 is mounted on plunger body 18 adjacent to distal end 20. The tissue debris catching and holding means will be discussed in greater detail below. Means 48 captures and holds tissue debris associated with punching a hole in a patient's tissue during a bypass procedure. The tissue debris held in means 48 is positively held and is located outside the patient.

A tissue punch 50 is mounted on cross pin 36 via spring rest 44 and remains stationary with respect to housing 12 while body 18 moves past the punch in directions 38 and 40. Punch 50 includes a proximal end 51 at rest 44 and a head 52 on a distal end thereof. Head 52 has a circular outer perimeter shape with a diameter essentially equal to but slightly smaller than the inner diameter of bore 28 so cutting edge 26 will move past head 52 as plunger body 18 moves in directions 38 and 40. Means 48 is mounted on body 18 and moves past head 52 as indicated in FIG. 3. As means 48 passes by head 52, any tissue debris on head 52 is captured and held by means 48. Plunger body 18 is adapted to move between a first configuration shown in FIG. 1 with cutting edge 26 spaced proximally of head 52 and a second configuration shown in FIG. 3 cutting edge 26 spaced distally from head 52 and head 52 located in bore 28.

Figure 1:
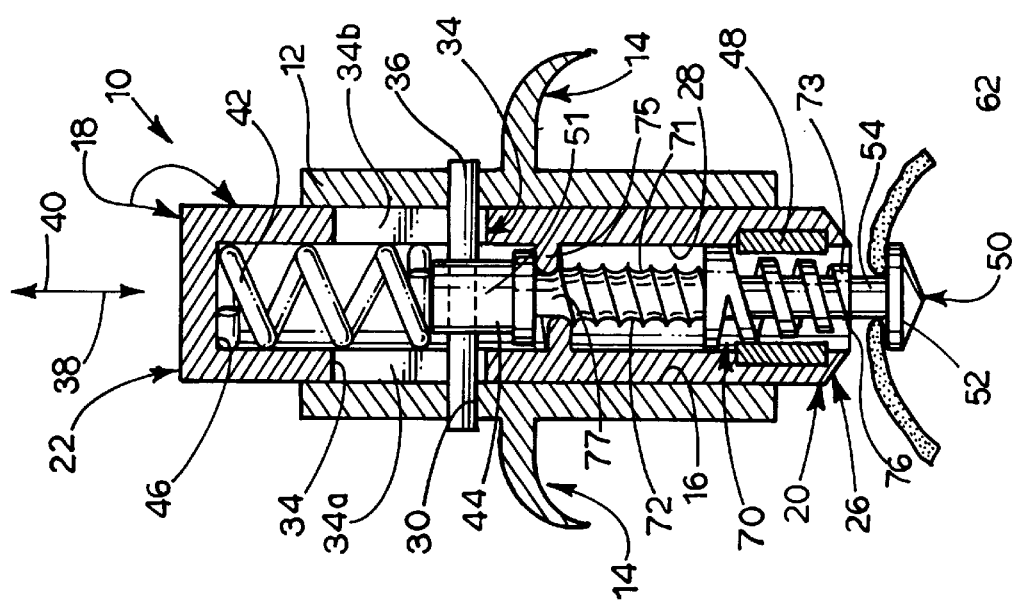
FIG. 1 is a cut away elevational view of a first form of the tissue punch embodying the present invention in a first configuration.

As device 10 is moved from the first configuration to the second configuration, cutting edge 26 moves by head 52 as can be understood by comparing FIGS. 1, 2 and 3. As cutting edge 26 passes head 52, a shearing force will be applied to any element, such as tissue 62, interposed between head 52 and edge 26. The shearing force cuts the tissue and defines a hole 64 in the tissue and forms tissue debris 66 on head 52. Debris 52 must be removed from the punch site and retained away from that site for the reasons discussed above.

Accordingly, device 10 includes a positive tissue debris capturing means 70 which includes body 71 that has a hollow central bore slidably receiving punch body 54 and which is located in bore 28. As shown in FIGS. 1–4, means 70 includes a helical thread 72 on body 71 and a helical transfer sleeve 73 on a distal end thereof adjacent to punch head 52 and a shoulder 74 on a proximal end thereof adjacent to a drive element 75 on body 18. Sleeve 73 has a distal tip 76 spaced from head 52 when device 10 is in the first configuration shown in FIG. 1 whereby tissue 62 can be interpositioned between tip 76 and head 52 and is mounted so head 52 engages that tip during device movement from the FIG. 1 position to the FIG. 3 position thereby locating tissue debris 66 against the helix of sleeve 73 as shown in FIG. 2. Sleeve 73 is mounted to then move the tissue debris away from head 52 as the device moves into the FIG. 3 position. As the device is moved so body 18 moves to locate head 52 in the FIG. 1 position, the tissue debris is trapped by means 48 and is held in body 18.

As can be seen in FIGS. 1–3, helical thread 72 engages element 75 and body 71 has a shank portion 77 that is free of helical thread. As body 18 moves past punch 50, element 75 engages helical thread 71 and causes sleeve 70 to rotate, in one direction when body 18 moves in direction 38 and in a reverse direction when body 18 moves in direction 40. This causes transfer sleeve 73 to rotate in corresponding directions. The rotation of sleeve 73 will move any tissue debris thereon away from punch head 52 as can be understood by comparing FIGS. 2 and 3. Because shank portion 77 does not have any helical thread thereon, when body 18 is in a position that located element 75 adjacent to shank portion 77, no rotation of sleeve 70 occurs. When the device is in between the FIG. 3 position and the FIG. 1 position, body 71 locates shank 77 adjacent to element 75 whereby element 75 drives sleeve 70 to move distal tip 76 away from head 52 to define the spacing shown in FIG. 1 for accommodating tissue 62 as above discussed.

Another means for operating drive sleeve 70 includes a one-way drive mechanism 80 shown in FIG. 4a. Mechanism 80 replaces drive elements 75. As can be understood from FIGS. 1–3 and 4a, since punch body 54 is attached to cross pin 36 which is mounted on housing 12 which is stationary with respect body 18, as plunger body 18 is moved in direction 38, body 18 will move past punch body 54 while spring 42 is being compressed into the FIGS. 2 and 3 conditions. Mechanism 80 includes pawls 82 pivotally mounted on body 18 with springs 84 biasing distal ends 86 of pawls 82 radially inward of bore 28 in direction 87 and into engagement with helical thread 71 on body 70. When body 18 moves in direction 38, pawl ends 86 will drag sleeve 73 in direction 38 until sleeve 73 engages punch head 52 at which time ends 86 ride over thread 71. When body 18 moves in direction 40, pawl ends 86 remain engaged with thread 71 causing rotation of sleeve 73. Because debris 66 is in frictional contact with the inside surface of body 18, rotation of sleeve 73 drives debris 66 further upwards into bore 28 as can be seen by comparing FIGS. 2 and 3 and spaces the debris from head 52. Head 52 is located above tissue capturing means 48 in the FIG. 3 position and thus debris 66 is also located above means 48. Rotation of sleeve 73 begins as soon as body 18 begins to move in direction 40 which occurs after head 52 has been drawn into bore 28 (the FIG. 3 position). At the end of the return stroke, ends 86 are in abutting contact with shoulder 87. At this point, further return movement of body 18 in direction 40 draws body 71 in direction 40 which separates distal end 76 of sleeve 71 from head 52 thereby establishing the gap between the sleeve and the head shown in FIG. 1. The shank portion of sleeve 71 is sized to establish the gap size desired. Spring 42 assists in the return movement and such return movement is initiated when body 18 abuts cross pin 36 adjacent to slots 34a and 34b. Other rotation devices can be used without departing from the scope of this invention, just so debris is moved away from head 52 before that head exits body 18 during the return movement thereof.

Figure 24:
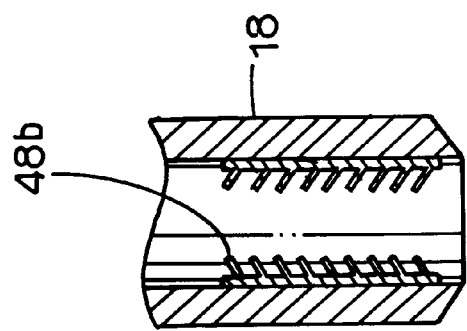
FIG. 24 shows one form of the means for trapping and holding tissue debris in the punch.

As can be understood from the foregoing, device 10 uses a helical debris transfer element that scoops up debris and holds it captive thereby preventing it from reentering the patient's body. The transfer sleeve rotates around the translating punch shaft in a given area within the punch body to scoop the tissue debris in the helix and trap it in means 48, such as brushes or brush-like bristles. This provides a positive means for capturing the debris, transferring and maintaining it inside the body of the punch without the chance of reentering the patient's bloodstream. This eliminates the step of cleaning the debris from the punch plunger. The preferred form of device 10 has means 48 comprised of stationary flexible plastic brushes located within the plunger body and located diametrically opposite to each other to positively trap the debris while the helix rotates with the debris past the brushes. While a solid showing of means 48 is disclosed in FIGS. 1–4, this is for the sake of drawing convenience. In actuality, this form of means 48 is a multiplicity of brush-like bristles such as are shown in FIG. 24.

In use, the surgeon will perform the initial incision and punching for the arteriotomy in exactly the same manner as he has been trained on prior art systems. However, when the punch is removed from the lumen to check for debris, the helix will have completed its rotation and the debris will have been moved away from the punch head and will have been trapped between the helix and the stationary flexible brushes and will not return outside the instrument. In this manner, the surgeon is reassured that the debris created in the punching operation will not enter the patient's bloodstream. Punch 10 is inserted into the lumen through a small linear incision made with a scalpel blade. The surgeon will then hold the grip housing 12 in the same manner as a syringe with his fingers supporting the half round finger protrusions 14 and his thumb on the proximal end 22 of plunger body 18 while the punch and the grip housing will remain stationary with respect to the plunger body as the distal end of the plunger body will approximate the tissue 62 to the punch.

At this time the surgeon will feel the tissue trapped between the punch and the plunger body ready to be cut. As indicated in FIG. 2, once enough pressure is applied from the surgeon to the proximal end of the plunger body, the distal end of the plunger body will pass by the punch thereby shearing the tissue that was trapped. At that time, the drive element 75 (or other such element as discussed above) which is integral to body 18 will cause rotation of body 71 and sleeve 73 while there is relative linear movement between body 18 and the punch. When the tissue debris 66 has been sheared from the lumen and is free in the body of the plunger it will be scooped up by the rotation of the helical transfer sleeve and will be trapped by stationary means 48 that is attached to the inside of plunger body 18. At the end of the stroke when cross pin 36 which holds the punch to the housing has bottomed out on the plunger body slot, the tissue debris will have rotated one full rotation around the punch via the helix transfer mechanism and will be trapped in stationary means 48. Once the surgeon releases the plunger body, return spring 42 will push the punch and means 48 through the drive element, such as element 75 or 80, which is integral to the plunger body 18. As discussed above with reference to FIG. 4a, element 80 is stationary with respect to body 18 which moves in directions 38 and 40 under influence of the surgeon and the return spring 42 respectively. As body 18 moves in direction 38, followers 86 ratchet over helical thread 71 and no rotation of the sleeve occurs. However, on the return stroke, in direction 40, the followers remain engaged with thread 71 and cause rotation of the sleeve. This rotation moves the debris away from the punching site and into engagement with means 48 spaced from the site as indicated in FIGS. 3 and 4. The tissue debris 66 as shown in FIG. 4 will remain trapped by means 48 that is attached to the inside wall of the plunger body. Cross pin 36 will bottom out on plunger body slot 34 and the cycle will be complete. Now the surgeon is ready to make another punch without having to remove the instrument from the surgical field to find and remove tissue debris.

As discussed above, the surgeon needs to be assured that once placed, the punch will not move causing misalignment and a potential leak site. The punch of the present invention provides this assurance.

Other means for capturing and positively moving tissue debris are shown in FIGS. 5–8. As shown in FIGS. 5–8, instrument 10' includes a plunger body 18 which is moved in directions 38 and 40 by the surgeon and return spring 42 respectively as discussed above. A cross pin 36 is attached to grip housing 12 and extends transversely across bore 16 of housing 12 and supports a plunger body 100. Pin 36 also extends through slot 34 of body 18 so plunger body 18 moves with respect to housing 12 as discussed above. Distal end 20 of housing 18 includes a cutting edge 26 as also discussed above.

A punch 50 has a punch head 52 which is circular in cross section and has an outer diameter sized to slide past cutting edge 26 when body 18 is moved far enough in direction 38 to pass head 52 as indicated in FIGS. 6 and 7 whereby tissue 62 trapped between punch head 52 and cutting edge 26 will be sheared as indicated in FIG. 6. This forms tissue debris 66 which must be captured in the body 18 and spaced from the tissue shearing site to ensure that such tissue debris will not reenter the patient's bloodstream.

A tissue trapping means 48' is included with instrument 10'. Trapping means 48' includes a flexible barbed element 102 fixedly attached to body 18 to move therewith with respect to punch 50'. Element 102 includes a flexible body 104 having a plurality of one-way barbs 106 thereon which taper from a base 108 toward a tip 110 located distally of the base with a main base 112 being located proximally of a main tip 114 and fixed to body 18. Body 104 is flexible so it will flex when it engages head 52 of the punch. Body 104 is shaped to flex tip 114 outwardly as indicated in FIG. 6 upon such engagement between tip 114 and head 52. This engagement and outward flexing will scoop debris 66 up and lift it away from the shearing site.

Means 48' further includes a barbed element 120 on the inside wall of body 18. Element 120 has one-way barbs 122 which taper from a tip 124 to a base 126 in a direction opposite to the taper of barbs 110 on element 102. This opposite taper permits the tip 114 to move past barbs 122 to move debris 66 away from the shearing site as body 18 moves past plunger 50 as indicated in FIGS. 6 and 7. The flexible nature of element 102 permits that element to resume its FIG. 5 condition when the plunger body is returned to its FIG. 5 position. However, the tissue debris will be held in place on barbs 122 as punch 10' returns to its FIG. 5 configuration. Element 102 is sized and positioned on body 18 to define a gap 123 between the distal end thereof and head 52 of punch 50'. Gap 123 is sized to accommodate tissue 62 and corresponds to the gap discussed above in reference to FIGS. 1 and 4a.

Device 10' provides a positive means for capturing the debris, transferring and maintaining it inside the body of the instrument. In use, the surgeon will perform the initial incision and punching for the arteriotomy in exactly the same manner as has he has been trained. However, when the instrument is removed from the lumen to check for debris, the tissue debris will be trapped between the flexible barbed diaphragm and the integral ratchet teeth.

Yet another punch that positively removes tissue debris from the shearing site and captures it is shown in FIG. 9 as device 10". Device 10" is similar to device 10' except that lifting ferule 120 replaces flexible barbed diaphragm 102. Tissue lifting ferule 120 is connected to an outer tube 122 which rides along an inner tube 124. When pressure is applied to finger rings 126, plunger tip 128 and tissue lifting ferule 120 are moved past plunger body 130 shearing the tissue that was loaded in the device as discussed above. Once an inner tube pin 132 makes contact with an inner release ramp 134 located on the inside of plunger body 130, inner tube 124 will rotate and ride in a lost motion slot 140 of outer tube 122. This will enable tissue lifting ferule 120 to move independently of inner tube 124 lifting the tissue debris farther into plunger body 130. Once tissue is pulled into plunger body 130 it will become trapped on tissue catching means 48", such as comb-like or bristle-like elements 142, which is located on the inside of plunger body 130. Inner tube return spring 146 is fully compressed when tissue lifting ferule 120 is in position to deposit tissue debris in means 48". When spring 146 is fully compressed, tissue lifting ferule 120 will be returned to the home state which re-arms the device.

As can be understood with reference to FIG. 9, pin 132 is connected to tube 124. Outer tube 122 covers the inner tube and has lost motion slots 140 defined therein. When the tissue is being punched (that is, at the moment of the cut), inner tube 124 and outer tube 122 are moving together with the topmost edge of the outer tube pushing on the pin 132. When the plunger has sheared the tissue and is moving within the plunger body the inner tube pin makes contact with the inner release ramp 134, which is inside the plunger body. This causes the inner tube and the inner tube pin to rotate until the pin falls into the lost motion slot of the outer tube. The outer tube is spring loaded causing the slot to bottom out on the pin. This action lifts the tissue lifting ferule.

In use, the surgeon will perform the initial incision and punching for the aortatomy in a desirable manner. However, when the punch is removed from the lumen to check for debris, the debris-lifting ferule will remain up in the body of the instrument, which is constructed of clear or translucent material, such as plastic, so that the ferule can be viewed. This allows the surgeon or nurse to verify that the debris is trapped within the body of the instrument.

The tissue lifting ferule additionally has small grooves 150 which correspond to the tissue trapping features on the interior surface of the body of the instrument. As tissue is brought up by the ferule into the central body of the instrument, it will become trapped and intertwined between the features 142. As the ferule is returned to its most distal position against plunger tip 128, the tissue debris stays lodged in the features and does not return outside of the instrument. In this manner, the surgeon is reassured that the debris created in the punching operation will not enter the patient's bloodstream.

Figure 13A:
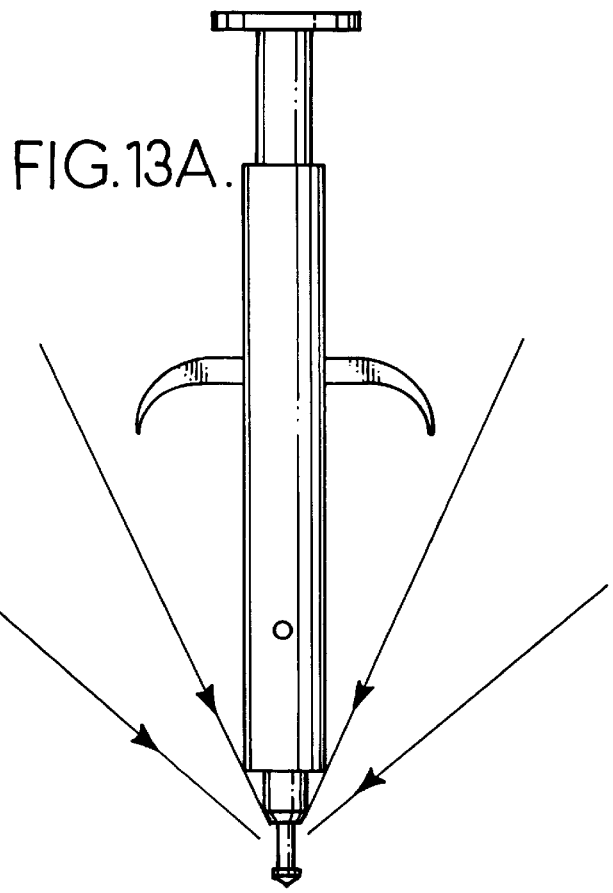
FIG. 13a illustrates sight lines for the punch of the present invention.
Figure 14:
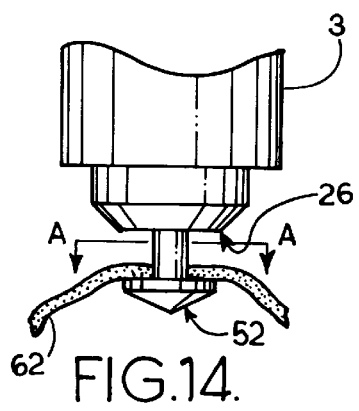
FIG. 14 illustrates a prior art tissue punch.
Figure 15:
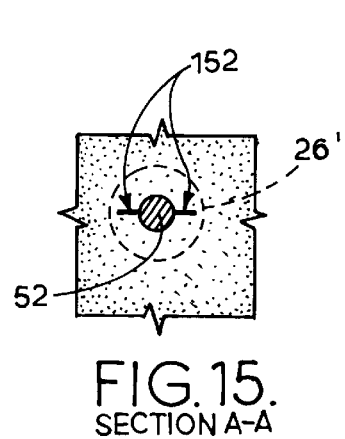
FIG. 15 illustrates proper alignment along line A—A of FIG. 14.
Figure 16:
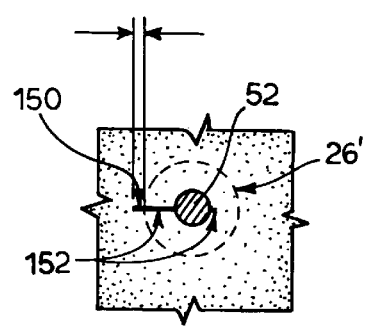
FIG. 16 illustrates improper alignment along line A—A of FIG. 14.

As discussed above, it is important to be sure that the punching operation is accurately located with respect to the incision. Accordingly, the present invention includes means for accurately locating the punch. Referring to FIGS. 11–16, it can be seen that improper location of the punch will lead to an extension 150 of the incision 152 past the punch hole (see FIGS. 13 and 16); whereas, a proper location of the punch will lead to a proper punching operation with the punch hole located centrally of the incision, see FIGS. 12 and 15. As indicated in FIGS. 15 and 16, the orientation of cutting edge 26 with respect to the incision is critical to establishing a proper and leak-free anastomosis. The location of the cutting edge with respect to the punch head is indicated in FIGS. 15 and 16 by dashed line 26'. Means 160 on the punch device assists proper orientation of the tissue with respect to the punch and can be used in connection with any of the instruments described herein. Means 160 includes a spring-loaded atraumatic sleeve 162 having one end thereof on the distal end of the instrument adjacent to the cutting edge thereof and having another end thereof engaging tissue interposed the between punch head and the cutting edge. Sleeve 162 is cylindrical and has an outer diameter equal to the inner diameter of the cutting edge and the outer diameter of the punch head. As can be understood from FIG. 13a, sight lines are established between a surgeon and the operating site. FIG. 12 shows how the surgeon will see the relationship between the outside of spring-loaded sleeve 162 to the incision, or aortatomy 164. If the surgeon is not able to see the aortatomy protrude past the spring-loaded sleeve, he will be assured that the cut will yield a leak-free anastomosis. FIG. 13 shows what the surgeon will see if the aortatomy 164 protrudes past the spring loaded sleeve. This will result in a leaking anastomosis. The device of the present invention can be fitted with a spring loaded sleeve to hold tissue against the plunger giving the surgeon direct visualization of the cutting area. The spring loaded sleeve applies a small amount of pressure to the tissue trapped between the sleeve and the punch.

As discussed above, a surgeon will put the plunger in the aortatomy and apply pressure on the plunger to bring the body of the plunger into contact with the aorta before punching the hole. During the procedure, the surgeon may move or reposition the punch to get the proper alignment to the aortatomy. If the surgeon decides to reposition the punch with the known art, the aortic tissue may be traumatized due to the sharp edge of the plunger body. The problem with this is the plunger body has a sharp edge which contacts the tissue and pressing the plunger on the aorta may traumatize tissue. The devices using the spring loaded sleeve 162 will help locate the punch properly and thus overcome this problem. The spring-loaded sleeve will also hold the tissue taut on the plunger thereby making a cleaner cut without tearing or partially cutting the tissue. With the spring loaded sleeve, if a surgeon decides to reposition, the sleeve will apply a slight pressure with no trauma applied to the tissue. Not only does this solution yield a cleaner and more precise cut, but it also is less traumatic when repositioning than existing punches.

The spring-loaded sleeve is shown in place on each of the above-discussed devices in FIGS. 10, 17 and 18. With the sleeve 162 on device 10' in FIG. 10, on device 10 in FIG. 17 and on device 10" in FIG. 18.

The spring-loaded device 160 provides the surgeon with the ability to use the device to make clean and accurate cuts in the aorta. Since the plunger in prior devices is hidden, the surgeon has to guess the location of the plunger to the end of the aortatomy. FIG. 14 indicates how a surgeon will place the plunger into the aortatomy and center the plunger within the aortatomy. FIG. 15 shows if the surgeon is able to estimate correctly and get the plunger centered in the aortatomy, the results will be a leak-free anastomosis. FIG. 16 shows if the surgeon is not able to center the plunger there will be a potential for the aortatomy to extend past the plunger causing a leak in the anastomosis. During this process, the surgeon will activate the punch moving it towards the plunger body. As shown in FIG. 14, tissue traumatization is possible if the plunger is released without fully cutting the tissue. The tissue will be pinched between the plunger and the plunger body cutting edge possibly injuring tissue if the plunger body has not been fully deployed.

Figure 23:
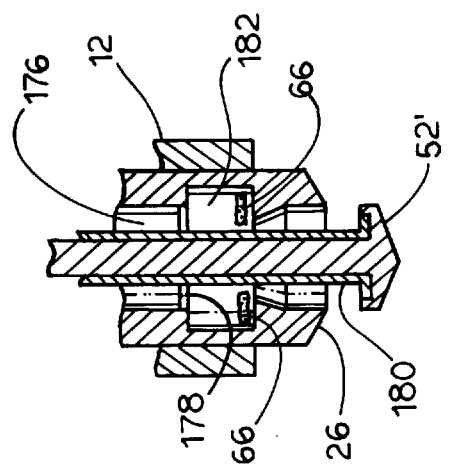
FIG. 23 shows the distal end of the FIG. 19 punch in the first configuration.
Figure 22:
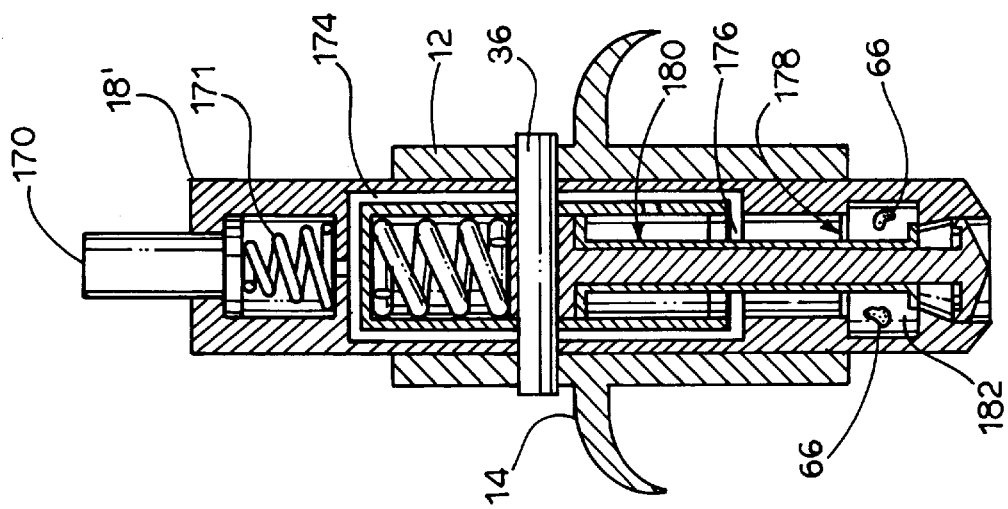
FIG. 22 shows the FIG. 19 punch in a second configuration.

Device 10''' shown in FIGS. 19–23 includes the use of suction to remove tissue debris from the cutting location and into the device. Suction is created from within device 10''' by pre-loading a vacuum plunger 170. As shown in FIG. 20, plunger 170 is depressed during activation of the device. In FIG. 21, the plunger is fully depressed activating the plunger body which moves the cutting edge 26 of the plunger body 18' to begin to shear tissue 62 against punch head 52'. In FIG. 22 after the tissue is punched the surgeon releases his pressure on vacuum plunger 170 which is spring loaded by spring 171 to open up and create a vacuum. Now, negative pressure travels through plunger body 18' via integral passages 174 and manifold 176 which are integral to plunger body 18'. At the distal end of manifold 176 are filters 178 which prevent loose tissue debris 66 from entering manifold 176 and clogging small passages 174. During this time, a spring-loaded lifting ferule 180 is activated pulling the tissue debris through a tortuous path at the distal tip of plunger body 18'. Now the tissue is trapped in a tissue chamber 182 and the vacuum pressure pulls the tissue debris off of lifting ferule 180 allowing the ferule to return to the home position free of tissue as shown in FIG. 23. It is noted that while negative pressure (vacuum) is sucking up the tissue debris, it also activates the lifting ferule through ports 183 to move the ferule off of the punch head and back onto that punch head to reset the instrument. Once the vacuum plunger has been activated the surgeon will perform the initial incision and punching for the aortatomy in the manner most desirable to him. However, when the punch is removed from the lumen to check for debris, the debris lifting ferule will move into the vacuum chamber and the surgeon will activate a switch to release the vacuum that has been stored by the initial plunger stroke. Now the tissue debris will be sucked into a designated chamber inside the plunger. This chamber can be made from a clear plastic that will allow the nurse to verify the debris is inside the device and not in any place that might jeopardize the safety of the patient. The vacuum is established within the instrument by elements associated with the instrument. Accordingly, no vacuum lines connected to vacuum sources will be needed, and the disadvantages associated with such lines will be avoided.

Figure 26:
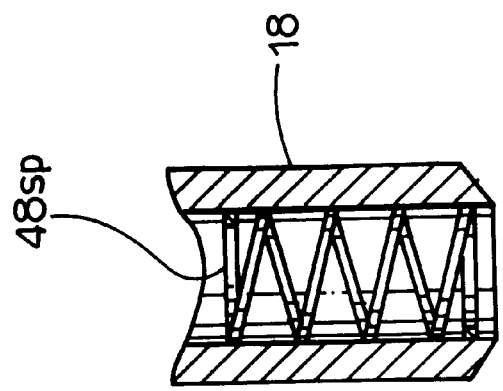
FIG. 26 shows yet another form of the means for trapping and holding tissue debris in the punch.
Figure 25:
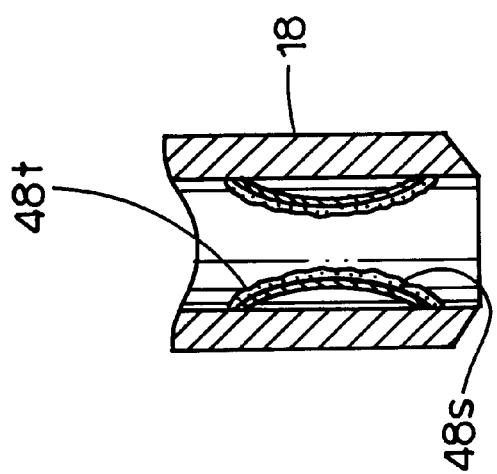
FIG. 25 shows another form of the means for trapping and holding tissue debris in the punch.

The tissue catching means can have several different configurations. As shown in FIG. 24, the means can include a flexible plastic one-way barb design 48B, or as shown in FIG. 25 at 48T it can include a spring wire with a tacky surface 48S bonded thereto, or as shown in FIG. 26 at 48C, it can include a compression spring 48SP wound from square stock. This creates a tortuous path that traps tissue debris.

It is understood that while certain forms of the present invention have been illustrated and described herein, it is not to be limited to the specific forms or arrangements of parts described and shown.

What is claimed is:

1. A tissue punching instrument comprising:

a housing;

a plunger body in said housing and movable with respect to said housing between a first position and a second position;

a tissue cutting element on said plunger body for movement therewith;

a tissue punching element fixed to said housing for shearing tissue trapped between said punching element and said tissue cutting element when said plunger body is moved between said first position and said second position;

tissue debris moving means connected to said plunger body for moving tissue debris associated with cutting tissue by said tissue cutting element and said tissue punching element away from a cutting location and into said plunger body; and means in said plunger body for trapping the tissue debris and holding the tissue debris spaced from the cutting location.

2. The tissue punching instrument defined in claim 1 wherein said tissue debris moving means includes a sleeve having a helical thread thereon.

3. The tissue punching instrument defined in claim 1 wherein said means for trapping the tissue debris includes brush-like elements mounted on said body.

4. The tissue punching instrument defined in claim 1 wherein said tissue debris moving means includes a flexible barbed element mounted on said body.

5. The tissue punching instrument defined in claim 4 wherein said tissue debris moving means further includes teeth on said body.

6. The tissue punching instrument defined in claim 1 wherein said means for trapping the tissue debris includes a spring wire with a tacky surface bonded thereto.

7. The tissue punching instrument defined in claim 1 wherein said means for trapping the tissue debris includes a compression spring.

8. The tissue punching instrument defined in claim 1 wherein said tissue debris moving means includes a vacuum source in said body.

9. The tissue punching instrument defined in claim 1 further including an alignment means on said body for guiding a surgeon in placing said tissue cutting element on a patient.

10. The tissue punching instrument defined in claim 9 wherein said alignment means includes a means for applying pressure to the tissue adjacent to said tissue cutting element.

11. The tissue punching instrument defined in claim 1 further including a lost motion means for connecting said tissue cutting element and said plunger body.

12. The tissue punching instrument defined in claim 2 further including a drive element mounted on said plunger body and engaging said helical thread.

13. The tissue punching instrument defined in claim 2 further including pawl elements mounted on said plunger body and engaging said helical thread.

14. The tissue punching instrument defined in claim 13 further including spring elements biasing said pawl elements into engagement with said helical thread.

15. The tissue punching instrument defined in claim 1 further including means for spacing said tissue moving means from a portion of said tissue punching element so tissue can be interposed between said tissue moving means and the portion of said tissue punching element to begin a punching operation.

16. The tissue punching instrument defined in claim 1 wherein said tissue moving means further includes a lifting ferule.

17. The tissue punching instrument defined in claim 1 wherein said tissue moving means further includes a lost motion means thereon.

18. A tissue punching instrument comprising:

a housing;

a plunger body movably mounted on said housing and movable with respect to said housing between a first position and a second position;

a tissue cutting element on said plunger body and which moves therewith;

a tissue punching element fixed to said housing which shears tissue trapped between said punching element and said tissue cutting element when said plunger body with said cutting element thereon is moved with respect to said housing with said punching element fixed thereto between said first position and said second position;

a tissue debris mover connected to said plunger body and which has a portion thereof which extends into a location to encounter tissue debris associated with cutting tissue by said tissue cutting element and said tissue punching element, said tissue debris mover being moved by the motion of the plunger body relative to said housing and which movement moves tissue debris encountered by the portion of said tissue debris mover away from a site at which said tissue is cut and into said plunger body; and a trap in said plunger body which is spaced from said location and is in position to receive tissue debris moved away from said location by said tissue debris mover and has an element thereon which traps the tissue debris and holds the tissue debris spaced from the site at which said tissue is cut.

19. The tissue punching instrument defined in claim 18 wherein said tissue debris mover includes a sleeve having a helical thread thereon.

20. The tissue punching instrument defined in claim 18 wherein said trap includes brush-like elements mounted on said body.

21. The tissue punching instrument defined in claim 18 wherein said tissue debris mover includes a flexible barbed element mounted on said body.

22. The tissue punching instrument defined in claim 21 wherein said tissue debris mover further includes teeth on said body.

23. The tissue punching instrument defined in claim 18 wherein said trap includes a spring wire with a tacky surface bonded thereto.

24. The tissue punching instrument defined in claim 18 wherein said trap includes a compression spring.

25. The tissue punching instrument defined in claim 18 further including a vacuum source in said body.

26. The tissue punching instrument defined in claim 18 further including a guide on said plunger body which is positioned to be viewed by a surgeon when placing said tissue cutting element on a patient.

27. The tissue punching instrument defined in claim 26 wherein said guide includes a biased element located to engage the tissue adjacent to said tissue cutting element.

28. The tissue punching instrument defined in claim 18 further including a lost motion element connecting said tissue cutting element and said plunger body.

29. The tissue punching instrument defined in claim 19 further including a drive element mounted on said plunger body and engaging said helical thread.

30. The tissue punching instrument defined in claim 19 further including pawl elements mounted on said plunger body and engaging said helical thread.

31. The tissue punching instrument defined in claim 30 further including spring elements biasing said pawl elements into engagement with said helical thread.

32. The tissue punching instrument defined in claim 18 further including an element on said tissue mover which spaces said tissue mover from a portion of said tissue punching element far enough so tissue can be interposed between said tissue mover and the portion of said tissue punching element to begin a punching operation.

33. The tissue punching instrument defined in claim 18 wherein said tissue mover means further includes a lifting ferule.

34. The tissue punching instrument defined in claim 18 wherein said tissue mover further includes a lost motion element thereon.

* * * * *